US006643394B1

United States Patent
Kuwabara (10) Patent No.: US 6,643,394 B1
(45) Date of Patent: Nov. 4, 2003

(54) VISUAL INSPECTION APPARATUS AND METHOD

(75) Inventor: Masayuki Kuwabara, Mitaka (JP)

(73) Assignee: Tokyo Seimitsu Co., Ltd., Mitaka (JP)

( * ) Notice: Subject to any disclaimer, the term of this patent is extended or adjusted under 35 U.S.C. 154(b) by 0 days.

(21) Appl. No.: 09/315,136

(22) Filed: May 20, 1999

(30) Foreign Application Priority Data

May 27, 1998 (JP) .......................................... 10-145806

(51) Int. Cl.$^7$ ................................................. G06K 9/68
(52) U.S. Cl. ...................................... 382/149; 382/144
(58) Field of Search ................................. 382/144, 145, 382/149, 219, 318, 319; 348/87, 126; 356/237.4, 237.5; 438/16; 250/559.39, 559.41, 559.45, 559.48

(56) References Cited

U.S. PATENT DOCUMENTS 3,963,354 A  *  6/1976  Feldman et al. ............. 356/168
4,771,468 A  *  9/1988  Batchelder et al. ............ 382/8
6,020,957 A  *  2/2000  Rosengaus et al. ......... 356/237.4

FOREIGN PATENT DOCUMENTS

JP          A-2-210249 A        8/1990  .......... G01N/21/88

OTHER PUBLICATIONS

Translation of Japanese Patent Publication JP 2–210249 A, to Taniguchi et al., published on Aug. 21, 1990, Translated by the USPTO, translation pp. 1–19.*

* cited by examiner

Primary Examiner—Brian Werner
(74) Attorney, Agent, or Firm—Oliff & Berridge, PLC (57) ABSTRACT

A plurality of chips arranged in the same scanning row of a wafer is divided into groups, which include a predetermined number of chips. The images of the chips in each group are compared with each other in the double detection. If one group includes the first the second and the third chips; the first chip and the second chip are compared, then the first chip and the third chip are compared, and at last, the second chip and the third chip are compared while the images are captured. It is therefore possible to detect the defects in the double detection for all the chips including peripheral chips by comparing the images for the same number of comparison times as the number of chips.

5 Claims, 7 Drawing Sheets

| ROW NUMBER | SCANNING NUMBER | CHIP NUMBER OF WHICH IMAGE IS BEING CAPTURED | COMBINATION OF IMAGES SUBJECT TO COMPARISON |
|---|---|---|---|
| 1 | S1 | C1 | NO COMPARISON |
| | | C2 | S1-1 & S1-2 |
| | | C3 | S1-1 & S1-3 |
| | | C4 | S1-2 & S1-4 |
| | | C5 | S1-3 & S1-5 |
| | S2 | C5 | S1-4 & S1-5 |
| | | C4 | S2-5 & S2-4 |
| | | C3 | S2-5 & S2-3 |
| | | C2 | S2-4 & S2-2 |
| | | C1 | S2-3 & S2-1 |
| | S3 | C1 | S2-2 & S2-1 |
| | | C2 | S3-1 & S3-2 |
| | | C3 | S3-1 & S3-3 |
| | | C4 | S3-2 & S3-4 |
| | | C5 | S3-3 & S3-5 |
| 2 | S1 | C7 | S3-4 & S3-5 |
| | | C6 | S1-7 & S1-6 |
| | | C5 | S1-7 & S1-5 |
| | | C4 | S1-6 & S1-5 |
| | | C3 | S1-4 & S1-3 |
| | | C2 | S1-4 & S1-2 |
| | | C1 | S1-3 & S1-1 |
| | S2 | C1 | S1-2 & S1-1 |
| | | C2 | S2-1 & S2-2 |
| | | C3 | S2-1 & S2-3 |
| | | C4 | S2-2 & S2-3 |
| ... | ... | ... | ... |

| ROW NUMBER | SCANNING NUMBER | CHIP NUMBER OF WHICH IMAGE IS BEING CAPTURED | COMBINATION OF IMAGES SUBJECT TO COMPARISON |
|---|---|---|---|
| 1 | S1 | C1 | NO COMPARISON |
| | | C2 | S1-1 & S1-2 |
| | | C3 | S1-1 & S1-3 |
| | | C4 | S1-2 & S1-4 |
| | | C5 | S1-3 & S1-5 |
| | S2 | C5 | S1-4 & S1-5 |
| | | C4 | S2-5 & S2-4 |
| | | C3 | S2-5 & S2-3 |
| | | C2 | S2-4 & S2-2 |
| | | C1 | S2-3 & S2-1 |
| | S3 | C1 | S2-2 & S2-1 |
| | | C2 | S3-1 & S3-2 |
| | | C3 | S3-1 & S3-3 |
| | | C4 | S3-2 & S3-4 |
| | | C5 | S3-3 & S3-5 |
| 2 | S1 | C7 | S3-4 & S3-5 |
| | | C6 | S1-7 & S1-6 |
| | | C5 | S1-7 & S1-5 |
| | | C4 | S1-6 & S1-5 |
| | | C3 | S1-4 & S1-3 |
| | | C2 | S1-4 & S1-2 |
| | | C1 | S1-3 & S1-1 |
| | S2 | C1 | S1-2 & S1-1 |
| | | C2 | S2-1 & S2-2 |
| | | C3 | S2-1 & S2-3 |
| | | C4 | S2-2 & S2-3 |
| ⋮ | ⋮ | ⋮ | ⋮ |

F I G. 7 (A)

F I G. 7 (B)

VISUAL INSPECTION APPARATUS AND METHOD

BACKGROUND OF THE INVENTION

1. Field of the Invention

The present invention relates generally to a visual inspection apparatus and method, and more particularly to a visual inspection apparatus and method applied to find defects in patterns on a semiconductor wafer, a photo mask, a liquid crystal display, or the like.

2. Description of Related Art

Conventionally, two adjacent chips are compared to each other in order to inspect patterns on a semiconductor wafer, a photo mask, a liquid crystal display, or the like. In order to inspect the patterns, an image obtaining part, which is composed of an optical microscope and an imaging device such as a time delay and integration (TDI) sensor, obtains images of the patterns represented with multiple values while continuously scanning the object along the X-axis. The obtained images are stored in an image data storage part such as a memory. When two images in the corresponding areas on the adjacent first and second chips are obtained, sub-pixel alignment is performed for these two images at regular frame intervals, and the two images are compared with each other on a pixel-by-pixel basis. In this comparison, a pair of a pixel of the first image and the corresponding pixel of the second image that has a gray level difference in excess of a preset threshold is recognized as having a possibility of being defective. At this point in such single detection, it is not clear which chip of the first and second chips has a possibility of being defective, and thus, a differential image of the first and second images is temporarily stored in a defect detecting part as two values. The above-mentioned comparison is performed between the second chip and the third chip to obtain another differential image, which is collated with the differential image of the first and second chips. It is therefore possible to determine which chip of the first and second chips has a possibility of being defective. In this detecting method (double detection), it is possible to determine defective parts on the chips and improve the reliability of the results since the same chip is subjected to the comparison twice.

In the conventional method, however, the chips except end chips (peripheral chips) in the same row or column are compared with the adjacent two chips in the same scanning to thereby accurately detect the defects. Since there are no chips outside the peripheral chips, only the single detection can be performed for the peripheral chips. Thus, the unreliable inspection is performed, or the peripheral chips are not inspected at all.

There is a conventional image comparison method, which comprises the steps of rescanning only the peripheral chips, which have been detected as having a possibility of being defective in the single detection, and comparing those peripheral chips with the second chips to the inside from those peripheral chips in order to find whether the peripheral chips have a possibility of being defective. This method, however, is inefficient since it is necessary to rescan the peripheral chips. In order to eliminate the need for rescanning the peripheral chips, the images of the peripheral chips and the second chips to the inside from the peripheral chips are stored in an image storage part such as a memory, and the images of these chips are read from the image storage part on completion of the scanning to compare the images. This is also inefficient since the third chip must be compared three times with the first, second and fourth chips. An ordinary comparison unit has only the minimum capacity for processing the captured images within a set amount of time, and therefore, the extra comparison lowers the inspection speed. To solve this problem, only the image of the first chip may be stored in the memory until the completion of one scanning, and the images of the peripheral chips stored in the previous scanning are compared with one another while the image of the first chip is captured in the next scanning, thereby performing the double detection for all the chips. If the distance between the peripheral chips becomes longer with the increase in the diameters of the wafers, a slight variation in a manufacturing process will cause noise problems such as odd color. This deteriorates the inspection sensitivity. It is therefore desirable to compare the closest chips available.

Alternatively, in a scanning method of Japanese Patent Provisional Publication No. 2-210249, the last chip in each scanning row or column is compared with the first chip in the next scanning row or column to perform the double detection even for the peripheral chips. Since, however, the straightness in the scanning direction (the X-axis) is higher than the absolute position accuracy along the Y-axis, the difference of the images along the Y-axis is greater than that of the images of chips in the same scanning rows. To correct the difference of the images, the images are normally shifted by less than a pixel and laid upon one another (a sub-pixel alignment). In this case, however, there is always such a possibility that there is a difference of 0.5 pixel at the maximum. The more the difference is corrected in the sub-pixel alignment, the lower the defect defecting sensitivity becomes due to the deterioration of the captured images. Moreover, this method cannot be applied to the inspection for only one row or column.

SUMMARY OF THE INVENTION

In view of the foregoing, it is an object of the present invention to provide a visual inspection apparatus, which is capable of detecting defects efficiently and accurately for all the chips including peripheral chips in double detection by comparing images a minimum amount of times.

To achieve the above-mentioned object, the present invention is directed to a visual inspection apparatus, comprising: an imaging means for capturing images of at least three areas arranged in a line on an object; an image comparison means for dividing the areas into at least one group, each group including at least consecutive three of the areas; for designating one of the areas as a subject area and other two of the areas as comparison areas for the subject area, the comparison areas being in the same group with the subject area and within a predetermined distance from the subject area; and for comparing the image of the subject area with the images of the comparison areas; and a defect detection means for detecting a defect in the object in accordance with the comparison between the images of the areas by the image comparison means.

The visual inspection apparatus is preferably characterized in that: the image comparison means numbers the areas in each group along the line; if the subject area is odd-numbered and is not one of ends of odd-numbered areas in the group, the comparison areas are two odd-numbered areas closest to the subject area; if the subject area is one of the ends of the odd-numbered areas in the group, the comparison areas are one odd-numbered area and one even-numbered area closest to the subject area; if the subject area is even-numbered and is not one of ends of even-numbered areas in the group, the comparison areas are two even-numbered areas closest to the subject area; and if the subject area is one of the ends of even-numbered areas in the group, the comparison areas are one even-numbered area and one odd-numbered area closest to the subject area.

Preferably, the imaging means relatively scans the object along the line by one of a line sensor and a TDI sensor to sequentially capture the images of the areas.

The visual inspection apparatus of the present invention scans the object along the X-axis to sequentially capture the images of the areas with the same pattern, which are arranged along the X-axis. Then, the areas arranged along the X-axis are divided into a predetermined number of groups. In each group, two areas in a predetermined interval are respectively combined with one another so that each area can be combined with other two areas. The image of each area, which is captured by the imaging means, is compared with the images of the other two areas. It is therefore possible to compare the images of all the areas including both ends (the peripheral chips) in the double detection in the minimum amount of comparison times (the same as the number of areas arranged along the X-axis). In addition, the image of each area is compared to the images of the close areas, and thus, the defects can be detected accurately.

To achieve the above-mentioned object, the present invention is directed to a visual inspection method, comprising the steps of: capturing images of at least three areas arranged in a line on an object; dividing the areas into at least one group, each group including at least consecutive three of the areas; designating one of the areas as a subject area and other two of the areas as comparison areas for the subject area, the comparison areas being in the same group with the subject area and within a predetermined distance from the subject area; and comparing the image of the subject area with the images of the comparison areas to determine whether the subject area is defective.

The visual inspection method is preferably characterized in that: the designating step comprises the step of numbering the areas in each group along the line; if the subject area is odd-numbered and is not one of ends of odd-numbered areas in the group, the comparison areas are two odd-numbered areas closest to the subject area; if the subject area is one of the ends of the odd-numbered areas in the group, the comparison areas are one odd-numbered area and one even-numbered area closest to the subject area; if the subject area is even-numbered and is not one of ends of even-numbered areas in the group, the comparison areas are two even-numbered areas closest to the subject area; and if the subject area is one of the ends of even-numbered areas in the group, the comparison areas are one even-numbered area and one odd-numbered area closest to the subject area.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENT

This invention will be described in further detail by way of example with reference to the accompanying drawings.

Figure 1:
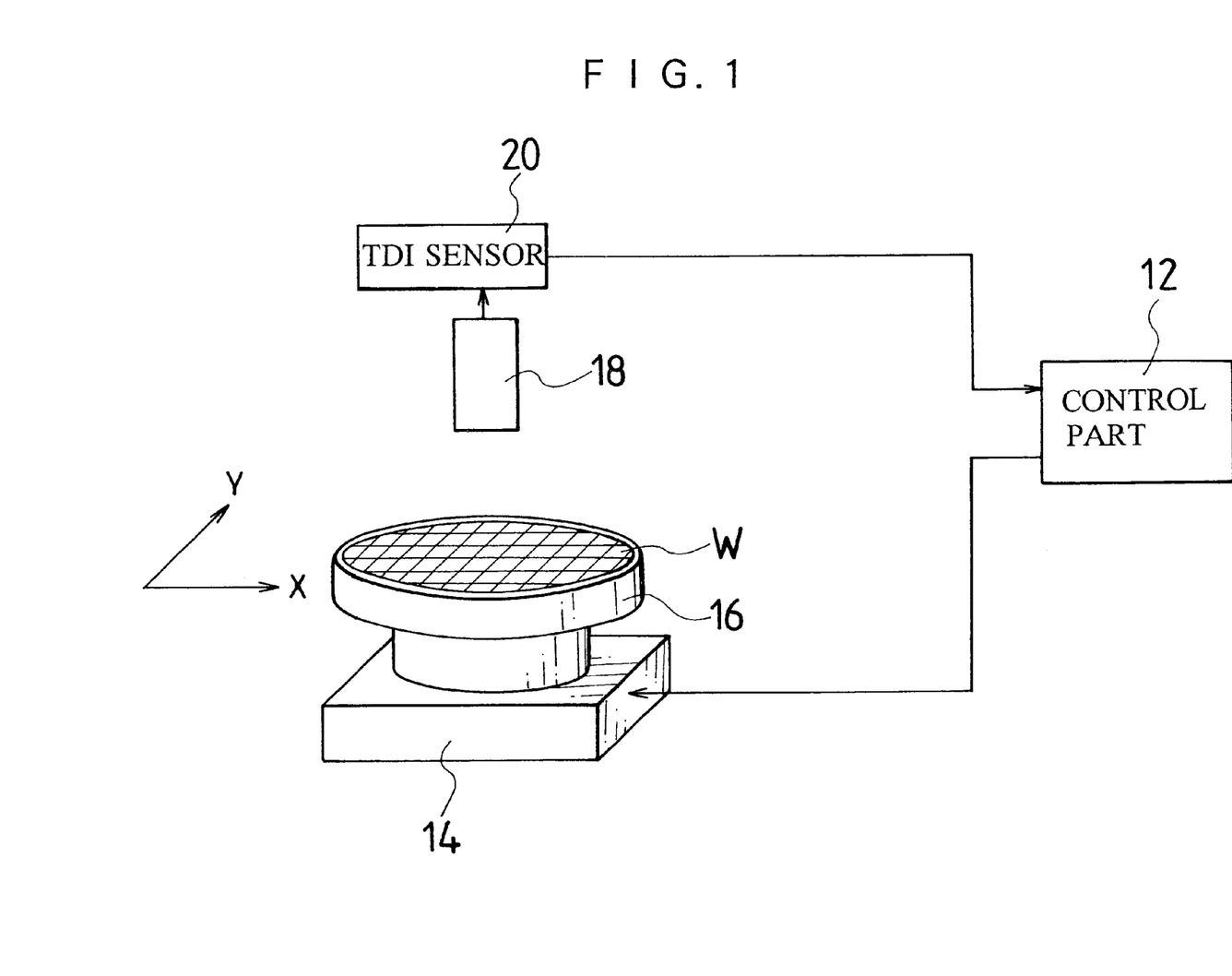
FIG. 1 is a view showing the entire structure of an embodiment of a visual inspection apparatus according to the present invention.

FIG. 1 is a view showing the entire structure of a preferred embodiment of a visual inspection apparatus, which determines whether each chip on a wafer contains a defective part or not. As shown in FIG. 1, the visual inspection apparatus comprises: a control part 12, which performs a variety of processing; an XY stage 14, which moves along X and Y axes horizontally under the control of the control part 12; a sample table 16 provided on the XY stage 14; a microscope 18 arranged above the sample table 16; and a TDI sensor 20 attached at the focusing position of the microscope 18.

A wafer W as an object is placed on the sample table 16. An image of the surface of the wafer W is enlarged and formed on an imaging surface of the TDI sensor 20 by the microscope 18.

As is well known, the TDI sensor 20 is a multistage sensor composed of one-dimensional line sensors such as charge-coupled device (CCD) line sensors. Signal electric charges accumulated in CCD elements of the line sensor at each stage are sequentially transferred to CCD elements of the line sensor at the next stage in synchronism with a scanning speed. Consequently, a plurality of CCD elements overlaps the signal electric charges at one point subject for imaging. Therefore, even if the electric charges are accumulated in each CCD element only for a short period, the signal electric charges at each point subject for imaging are amplified to make up for the shortage in the quantity of light. Thus, the TDI sensor 20 is able to scan the object at a higher speed than the ordinary single-stage CCD line sensor.

In the visual inspection apparatus of the embodiment, the TDI sensor 20 scans the surface of the wafer W along the X-axis. The TDI sensor 20 scans the surface image of the wafer W, which is moved by the XY stage 14 along the X-axis. In this embodiment, the TDI sensor 20 is used as the imaging means, but it is possible to use the ordinary one-dimensional sensor such as the CCD line sensor or a two-dimensional sensor.

Figure 2:
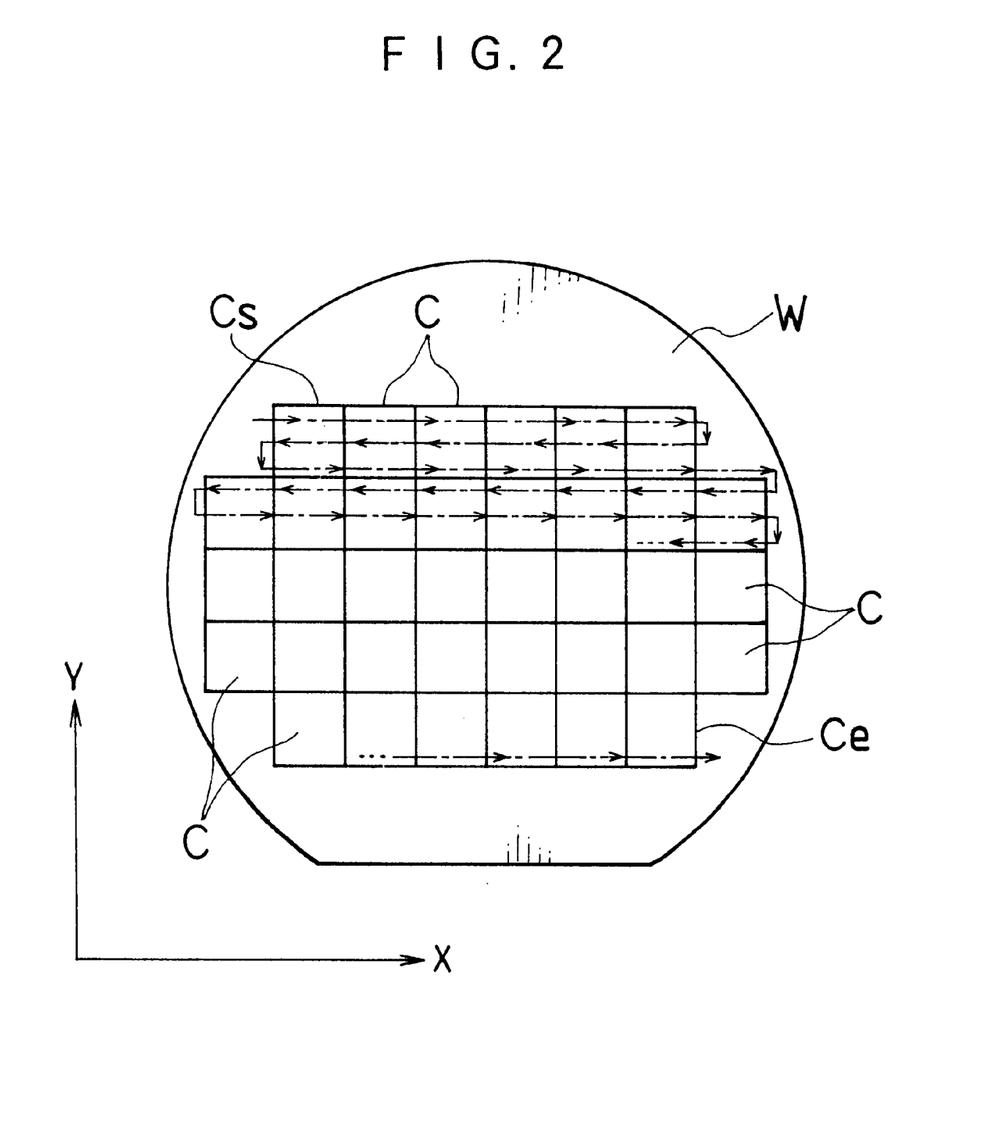
FIG. 2 is a view showing an example of a scanning track of a TDI sensor on a wafer.

The control part 12 controls the XY stage 14 to move the wafer W along the X and Y-axes. The control part 12 controls the TDI sensor 20, which relatively scans the wafer W, and obtains the surface image of the wafer W from the TDI sensor 20. FIG. 2 shows an example of a scanning track of the TDI sensor 20 on the wafer W under the control of the control part 12. As shown in FIG. 2, a number of chips C are regularly arranged along the X and Y-axes on the wafer W, and the chips have the same patterns. As indicated by a dashed and dotted line in FIG. 2, the TDI sensor 20 starts scanning the wafer W along the X-axis from the upper left corner of a chip $C_s$ on the highest row, and reciprocally scans the wafer W until it reaches a chip $C_e$ on the lowest row. The TDI sensor 20 shifts the scanning line along the Y-axis downward little by little (by the image reading width (scanning width) in a direction along the Y-axis perpendicular to the scanning direction along the X-axis) to complete the scanning for all the chips C arranged on the wafer W. The scanning is not necessarily performed on the scanning track in FIG. 2, but the scanning may also be performed in any other scanning tracks.

Then, the control part 12 sends the obtained surface image of the wafer W to a defect detecting part, which is a component of the control part 12. The defect detecting part detects a defective part in each chip on the wafer W.

Figure 3:
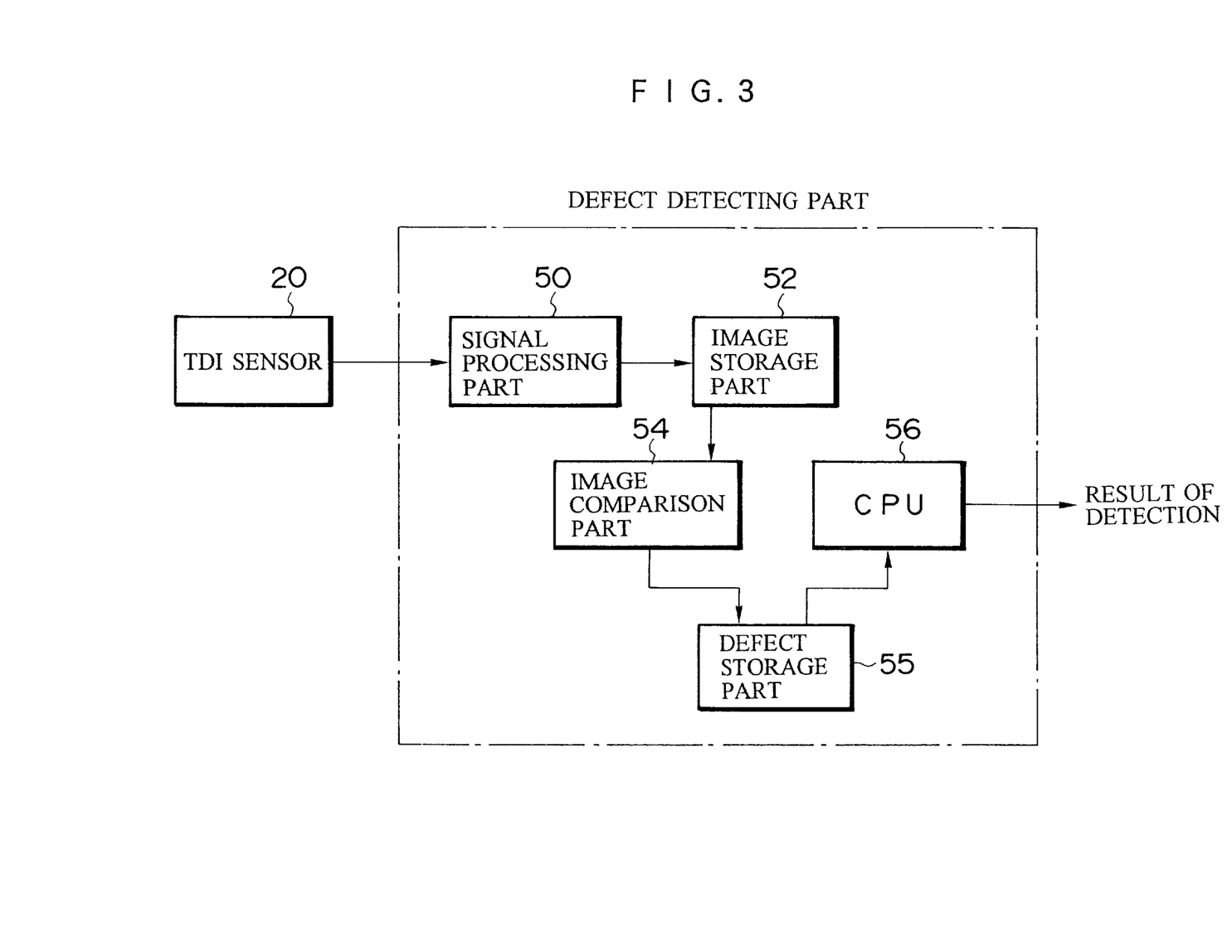
FIG. 3 is a block diagram showing an embodiment of a defect detecting part.

FIG. 3 is a block diagram showing an embodiment of the defect detecting part in the control part 12. As shown in FIG. 3, the defect detecting part comprises a signal processing part 50, an image storage part 52, an image comparison part 54, a defect storage part 55 and a CPU 56.

The signal processing part 50 receives image signals sequentially from the TDI sensor 20, and converts the image signals into digital image data. The signal processing part 50 outputs the image data to the image storage part 52.

The image storage part 52 is composed of a memory such as a RAM. The image data, which is outputted from the signal processing part 50, is sequentially stored in the image storage part 52.

The image comparison part 54 reads the image data sequentially from the image storage part 52, and compares the image data of two chips to determine whether the two chips have a possibility of being defective. The image comparison part 54 sends the results to the defect storage part 55.

The CPU 56 reads the two results for each chip and finds defective chips and their coordinates, and outputs the results to a monitor, etc.

Figure 4:
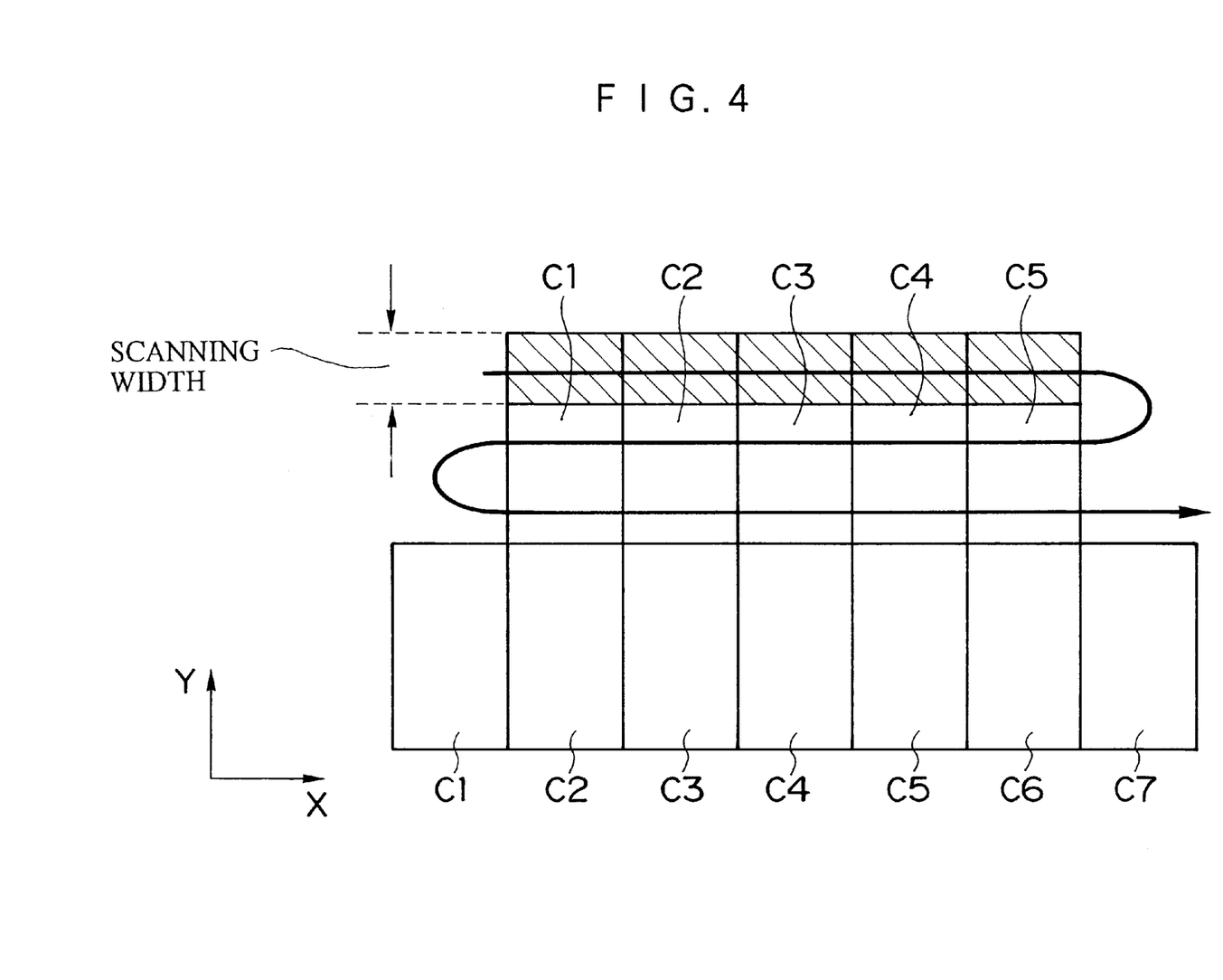
FIG. 4 is a view showing an example of the arrangement of chips on the wafer.
Figure 5:
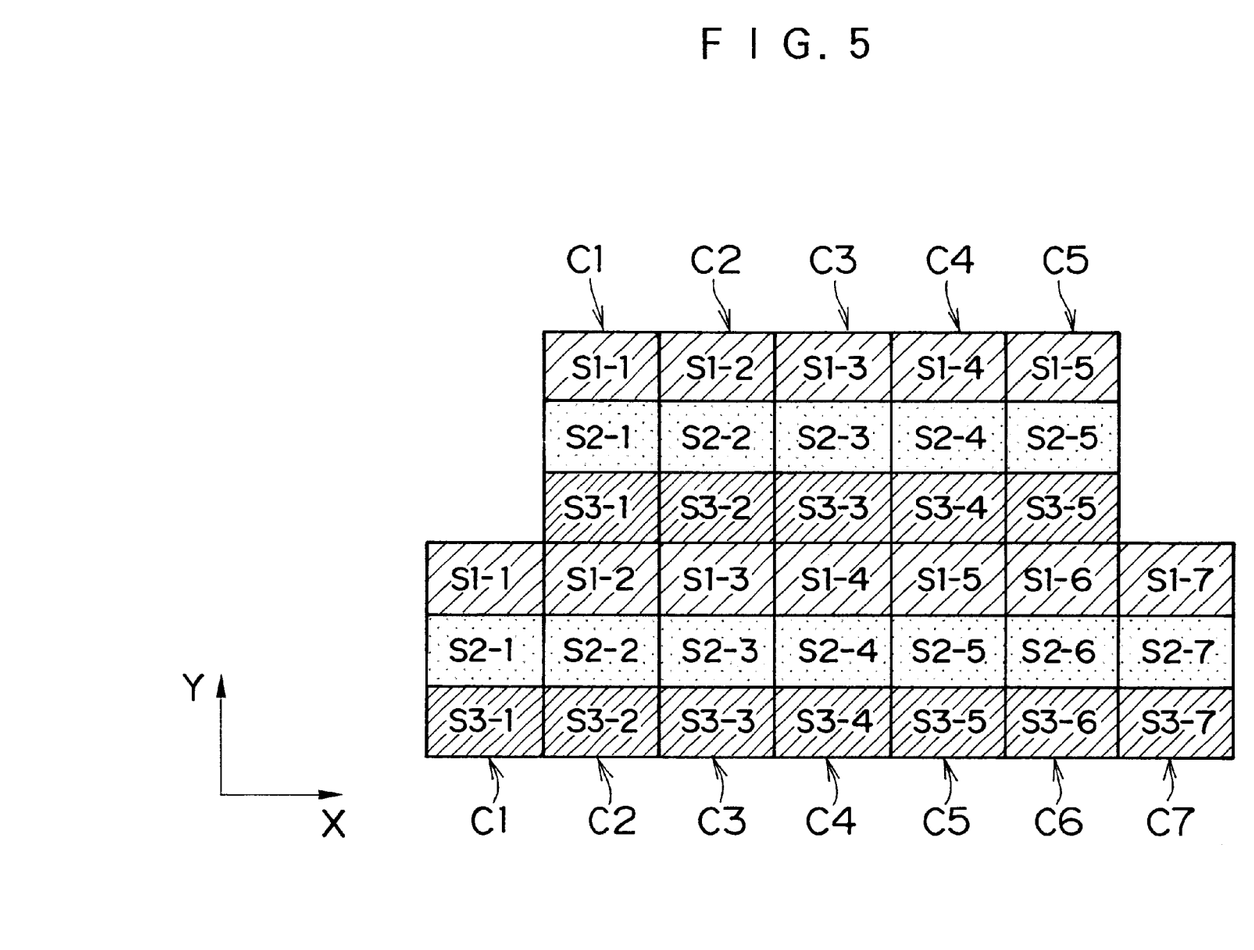
FIG. 5 is a view showing the areas in each chip, which are denoted by reference numerals.

A description will now be given of the operation of the defect detecting part. For example, five chips C1–C5 are arranged in the first row and seven chips C1–C7 are arranged in the second row of the wafer W as shown in FIG. 4. In this case, the TDI sensor 20 reciprocally scans the chips in a predetermined scanning width as indicated by an arrow in FIG. 4, and the images of the chips are sequentially captured into the image storage part 52 in accordance with the scanning track. In FIG. 5, the chips in the first and second rows in FIG. 4 are divided along the Y-axis at intervals of the scanning width, and the divided areas are denoted by reference numerals. "m" in the reference numeral "Sm-n" (m, n=1, 2, . . . ) indicates an order in which the TDI sensor 20 scans each area of each chip, and "n" indicates a row number of each chip (a chip number). "Sm" will be referred to as a scanning number. To reciprocally scan the wafer W as shown in FIG. 4, the TDI sensor 20 sequentially scans the areas S1-1, S1-2, S1-3, S1-4 and S1-5 of the chips C1–C5 arranged in the first row. After scanning the area S1-5, the XY stage is shifted along the Y-axis by the scanning width so that the TDI sensor 20 can continuously scan the areas S2-5, S2-4, S2-3, S2-2 and S2-1. This scanning is continued to capture the images of the wafer W as a whole into the image storage part 52.

Figure 6:
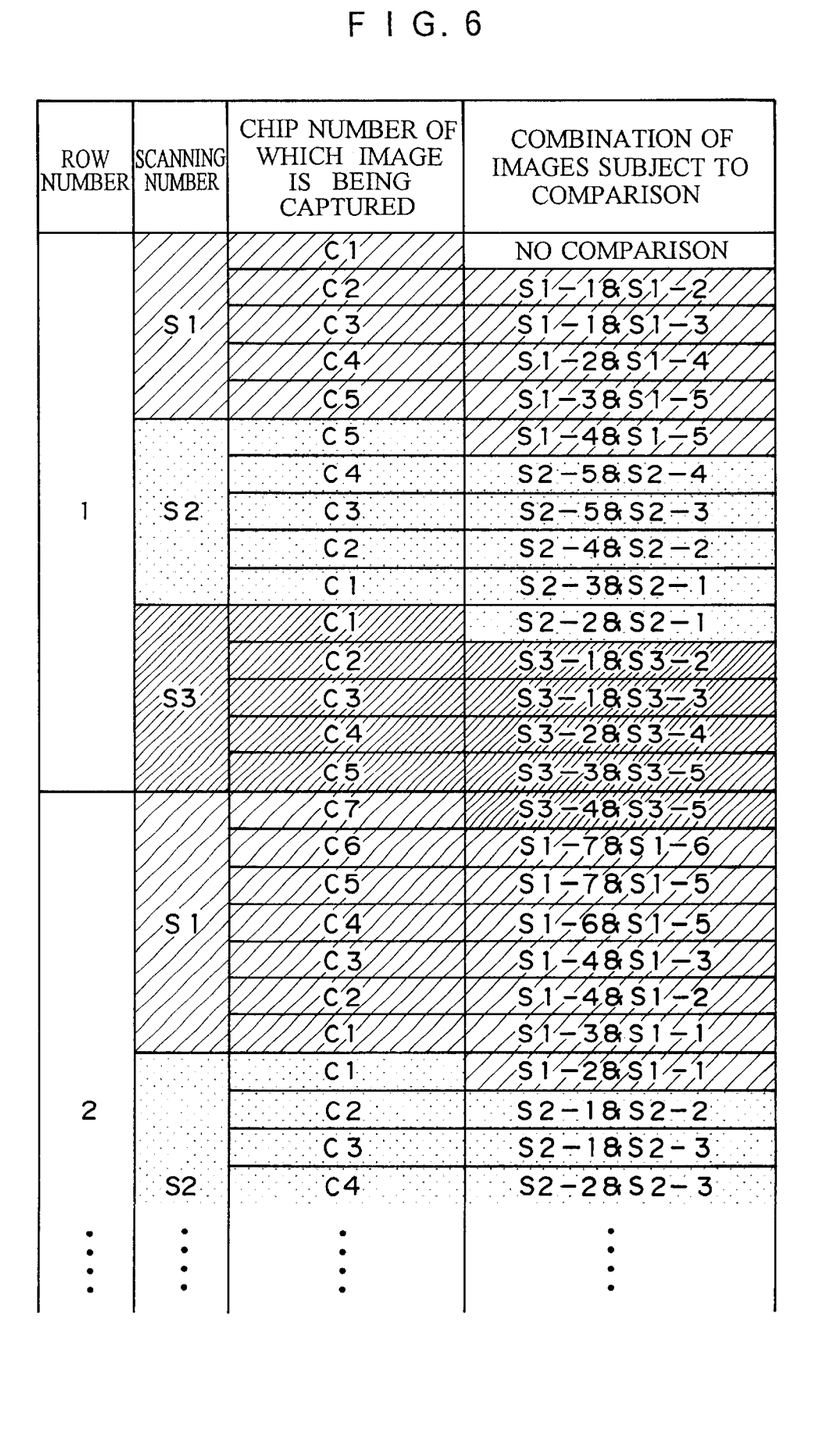
FIG. 6 is a view showing a relationship in time between the capture of images and the comparison of images.

While the TDI sensor 20 is capturing the images of the chips, the image comparison part 54 reads the images of the chips from the image storage part 52 in a predetermined order and compares the images of two areas. Referring to FIG. 6, while the TDI sensor 20 is capturing the image of the area S1-1 in the chip C1 on the first row, there is no image of another chip subject to comparison, and hence, the image comparison part 54 does not compare any images. When the TDI sensor 20 starts capturing the image of the area S1-2 in the chip C2, the image comparison part 54 compares parts of the image of the area S1-2 with the corresponding parts of the image of the area S1-1, which is read from the image storage part 52. If a difference between the parts of the images exceeds a predetermined threshold, the parts are determined as having a possibility of being defective, and the data relating to those images are temporarily stored in the defect storage part 55. For example, each of the images of the areas S1-1, S1-2, . . . , is divided into a predetermined number of frames, and the frames are read from the image storage part 52. The image comparison part 54 compares the images on a frame-by-frame basis.

When the TDI sensor 20 starts capturing the image of the area S1-3 of the chip C3, the image comparison part 54 compares the image of the area S1-3 with the image of the area S1-1, which is read from the image storage part 52. Since the image of the area S1-1 has been compared with the two areas S1-2 and S1-3 of the two different chips C2 and C3 (i.e., the double detection has been performed), the already-compared parts of the image of the area S1-1 are sequentially erased from the image storage part 52. If the same position in the area S1-1 is detected as having a possibility of being defective in both comparisons with the areas S1-2 and S1-3, the CPU 56 determines the area S1-1 as being defective.

When the TDI sensor 20 starts capturing the image of the area S1-4 of the chip C4, the image comparison part 54 compares the image of the area S1-4 with the image of the area S1-2, which is read from the image storage part 52. Since the image of the area S1-2 has been compared with the two different chips in the double detection, the already-compared parts of the image are sequentially erased from the image storage part 52. Then, the CPU 56 determines the presence of a defect in the area S1-2 as is the case with the area S1-1.

Likewise, when the TDI sensor 20 starts capturing the image of the area S1-5 of the chip C5, the image comparison part 54 compares the image of the area S1-5 with the image of the area S1-3. When the capturing of the image of the area S1-5 is completed, the TDI sensor 20 starts the next scanning S2. Since the double detection has not been performed for the areas S1-4 and S1-5 in the previous scanning S1, the image comparison part 54 compares the images of the areas S1-4 and S1-5 while the TDI sensor is scanning the area S2-5 in the scanning S2. Consequently, the double detection is performed for all the areas in the scanning S1. Since the areas S1-4 and S1-5 are compared while the image of the area S2-5 is captured in the scanning S2, at the corresponding time to the time when the image of the area S1-1 is captured and no comparison is performed, the scanning will not be delayed by the last comparison in the scanning S1.

In the above-described manner, the defects are detected by comparing the images sequentially in the scanning S1, S2, and S3. When the scanning S3 is completed, the double detection has not been performed for the areas S3-4 and S3-5. The double detection for the areas S3-4 and S3-5 is completed while the TDI sensor 20 scans the area S1-7 in the scanning for the chips C1–C7 on the second row.

More specifically, when each scanning is completed, the double detection is always incomplete for the last two chips in each scanning row. This, however, does not effect the inspection time since the double detection is performed for the last two chips in each scanning row while the TDI sensor 20 is capturing the first image in the next scanning row. On completion of the scanning for the entire wafer W, the double detection is incomplete for the last two chips in the last scanning row. This does not effect the inspection time since the double detection can be completed for the last two chips in the last scanning row within a negligible time, which is about the same as the time required for scanning one chip.

In the above explanation, there are five chips in one scanning row. If the number of the chips in one scanning row is any other, the processing is performed in a manner described below. The order in which the images are read from the image storage part 52 can be classified into the following three cases according to the number of chips in one scanning row: case 1 wherein the number of chips in one scanning row is 3n+3; case 2 wherein the number of chips in one scanning row is 3n+4; and case 3 wherein the number of chips in one scanning row is 3n+5 (n=0, 1, 2, 3, . . . ).

More specifically, the chips are made in groups of three from the top of the scanning row, and the chips in each group are referred to as the first chip, the second chip and the third chip. In each group, the first chip and the second chip are compared first, then the first chip and the third chip are compared, and at last, the second chip and the third chip are compared. Thus, the double detection is performed in each group. The comparison is completed for 3n chips in the above equation even if n is any natural number.

Considering the remaining chips for which the double detection is incomplete, in the case 1, there are three chips remaining, and these three chips can be read in the above-mentioned manner.

The case 2 is, for example, the case where the seven chips C1–C7 are arranged in the second row in FIG. 4. As for the remaining four chips, the first chip and the second chip are compared first, then the first chip and the third chip are compared, and the second chip and the fourth chip are compared, and at last, the third chip and the fourth chip are compared. In the case of the arrangement on the second row in FIG. 4, the remaining four chips are equivalent to the chips C4–C1 in the scanning S1 on the second row in FIG. 6.

The case 3 is, for example, the case where the five chips C1–C5 are arranged in the first row in FIG. 4. As for the remaining five chips, the first chip and the second chip are compared first, then the first chip and the third chip are compared, the second chip and the fourth chip are compared, the third chip and the fifth chip are compared, and at last, the fourth chip and the fifth chip are compared.

Comparing the images of the chips in the same scanning row in the above-mentioned manner detects the presence of defects for all the chips in the minimum comparison times, which are equal to the number of the chips.

In the above-mentioned comparison method, the images are compared between two chips that are close to one another by a twice as long as an interval between the adjacent chips or less, and therefore, the defects can be accurately detected.

In the above-mentioned comparison method, the chips in the same scanning row are compared with one another, and thus, this method may be applied to detect the defects in the chips in only one row.

In the above explanation, three chips make one group. If three or more chips are in one group, each chip can be compared twice. Thus, any number larger than two (three or more) of chips may make one group.

Figure 7:
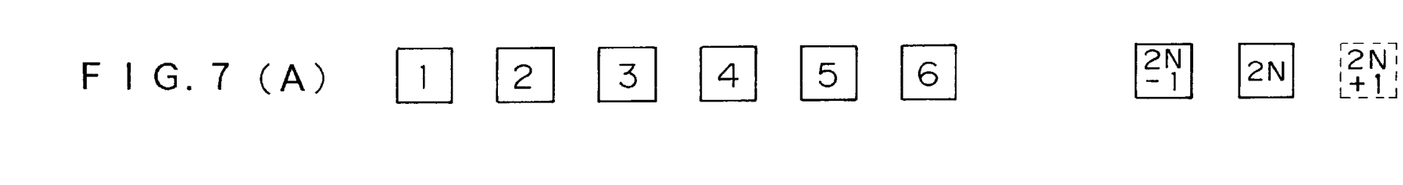
FIGS. 7(A) and 7(B) are views showing examples of combinations of chips subject to comparison.

A description will now be given of a preferred method for combining each of any number of chips with other two chips. If 2N (N=2, 3, 4, . . . ) chips from the first chip to the 2N-th chip are sequentially arranged as shown in FIG. 7(A), the 2N chips are divided into even-numbered chips and odd-numbered chips. As indicated by a solid line in FIG. 7(B), each chip is connected to the adjacent chips, and the chips are arranged like a closed loop. The images of the adjacent chips are compared in this arrangement. More specifically, each even-numbered chip is compared with two closest even-numbered chips, and each odd-numbered chip is compared with two closest odd-numbered chips. In this case, however, the odd-numbered chips at both ends (the first chip and the (2N−1)-th chip) and the even-numbered chips at both ends (the second chip and the 2N-th chip) are compared with adjacent chips among them. Consequently, each chip is compared with the close chips, which are next to the chip or the next chip but one. When the capturing of the image in one chip is completed, the image data subject to the next comparison is captured into the image storage part 52. Thus, the images can be compared with one another while the chips are scanned continuously. As shown by dotted lines in FIG. 7(B), if there are odd number (2N+1) of chips, the (2N−1)-th chip and the (2N+1)-th chip are compared with one another, and the 2N-th chip and the (2N+1)-th chip are compared with one another in stead of comparing the (2N−1)-th chip and the 2N-th chip.

In each group (the number of the chips is 3, 4 or 5) in the above-described cases 1, 2 and 3, the combinations of the chips subject to comparison are determined in the method shown in FIG. 7(B). Likewise, if the number of chips in one group is determined arbitrarily, the combinations of the chips subject to comparison can be determined in the method shown in FIG. 7(B). That makes it possible to perform the double detection by properly combining every chip with other two chips in the same scanning row without grouping the chips in the same scanning row.

The combinations of the chips are not necessarily determined in the method in FIG. 7(B). Two chips at a predetermined interval may be combined in each group, and each chip may be combined with other two chips. In other words, the closed loop of chips as shown in FIG. 7(B) is not necessarily arranged in the above-mentioned manner. If the distance between the first chip and the 2N-th chip is allowable in view of the image comparison accuracy in the case that the first to 2N-th chips are arranged as shown in FIG. 7(A), a closed loop is formed by arranging the first chip next to the 2N-th chip with the positional relationship between the first chip to the 2N-th chip being unchanged. The adjacent chips are combined in this arrangement. This method can be used if each group has a small number of chips.

In the above-described embodiment, the present invention is applied to the visual inspection apparatus that detects the presence of defects in the chips with the same pattern, which are arranged on the wafer. The present invention, however, may also be applied to a visual inspection apparatus, which inspects other object such as a photo-mask and a liquid crystal display.

As set forth hereinabove, the visual inspection apparatus of the present invention scans the object along the X-axis to sequentially capture the images of the areas with the same pattern, which are arranged along the X-axis. Then, the areas arranged along the X-axis are divided into a predetermined number of groups. In each group, two areas in a predetermined interval are respectively combined with one another so that each area can be combined with other two areas. The image of each area, which is captured by the imaging means, is compared with the images of the other two areas. It is therefore possible to compare the images of all the areas including both ends (the peripheral chips) in the double detection in the minimum amount of comparison times (the same as the number of areas arranged along the X-axis). Moreover, the images can be compared almost at the same time as the capture of the images. This improves the inspection efficiency and speed in the visual inspection. In addition, the image of each area is compared to the images of the close areas, and thus, the defects can be detected accurately.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A visual inspection apparatus, comprising:

imaging means for capturing images of four or more areas arranged in a line on an object, the line having areas at its peripheral ends;

image comparison means for dividing the areas into a plurality of groups, each group including at least consecutive three of the areas arranged in said line; for designating one of the areas as a subject area and other two of the areas as comparison areas for the subject area, the comparison areas being in the same group with the subject area and within a predetermined distance from the subject area; and for comparing the image of the subject area with the images of the comparison areas; and defect detection means for detecting a defect in the object in accordance with the comparison between the images of the areas by the image comparison means, wherein each area including each peripheral end, which is captured by the imaging means, is compared with the images of the other areas of the at least consecutive three areas as the subject area.

2. A visual inspection apparatus, comprising:

imaging means for capturing images of four or more areas arranged in a line on an object;

image comparison means for dividing the areas into a plurality of groups, each group including at least consecutive three of the areas arranged in said line; for designating one of the areas as a subject area and other two of the areas as comparison areas for the subject area, the comparison areas being in the same group with the subject area and within a predetermined distance from the subject area; and for comparing the image of the subject area with the images of the comparison areas; and defect detection means for detecting a defect in the object in accordance with the comparison between the images of the areas by the image comparison means, wherein:

the image comparison means numbers the areas in each group along the line, wherein the image comparison means is configured to select the comparison areas as follows:

when the subject area is odd-numbered and is not one of ends of odd-numbered areas in the group, the comparison areas are two odd-numbered areas closest to the subject area;

when the subject area is one of the ends of the odd-numbered areas in the group, the comparison areas are one odd-numbered area and one even-numbered area closest to the subject area;

when the subject area is even-numbered and is not one of ends of even-numbered areas in the group, the comparison areas are two even-numbered areas closest to the subject area; and when the subject area is one of the ends of even-numbered areas in the group, the comparison areas are one even-numbered area and one odd-numbered area closest to the subject area.

3. The visual inspection apparatus as defined in claim 1, wherein the imaging means relatively scans the object along the line by one of a line sensor and a TDI sensor to sequentially capture the images of the areas.

4. A visual inspection method, comprising the steps of:

capturing images of four or more areas arranged in a line on an object, the line having areas at its peripheral ends;

dividing the areas into a plurality of groups, each group including at least consecutive three of the areas arranged in said line;

designating one of the areas as a subject area and other two of the areas as comparison areas for the subject area, the comparison areas being in the same group with the subject area and within a predetermined distance from the subject area; and comparing the image of the subject area with the images of the comparison areas to determine whether the subject area is defective, wherein each area including each peripheral end, which is captured, is compared with the images of the other areas of the at least consecutive three areas as the subject area.

5. A visual inspection method, comprising the steps of:

capturing images of four or more areas arranged in a line on an object;

dividing the areas into a plurality of groups, each group including at least consecutive three of the areas arranged in said line;

designating one of the areas as a subject area and other two of the areas as comparison areas for the subject area, the comparison areas being in the same group with the subject area and within a predetermined distance from the subject area; and comparing the image of the subject area with the images of the comparison areas to determine whether the subject area is defective, wherein:

the designating step comprises the step of numbering the areas in each group along the line, wherein the comparison areas are selected as follows:

when the subject area is odd-numbered and is not one of ends of odd-numbered areas in the group, the comparison areas are two odd-numbered areas closest to the subject area;

when the subject area is one of the ends of the odd-numbered areas in the group, the comparison areas are one odd-numbered area and one even-numbered area closest to the subject area;

when the subject area is even-numbered and is not one of ends of even-numbered areas in the group, the comparison areas are two even-numbered areas closest to the subject area; and when the subject area is one of the ends of even-numbered areas in the group, the comparison areas are one even-numbered area and one odd-numbered area closest to the subject area.

* * * * *